(12) United States Patent
Sivakumar et al.

(10) Patent No.: US 7,459,553 B2
(45) Date of Patent: Dec. 2, 2008

(54) PROCESS FOR THE PREPARATION OF CARBOXAMIDE COMPOUNDS

(75) Inventors: Bobba Venkata Sivakumar, Navi Mumbai (IN); Shekhar Bhaskar Bhirud, Navi Mumbai (IN); Chandrasekhar Batchu, Navi Mumbai (IN); Sanjay Anantha Kale, Navi Mumbai (IN)

(73) Assignee: Glenmark Generics Ltd., Mumbai (IN)

( * ) Notice: Subject to any disclaimer, the term of this patent is extended or adjusted under 35 U.S.C. 154(b) by 600 days.

(21) Appl. No.: 11/077,723

(22) Filed: Mar. 11, 2005

(65) Prior Publication Data

US 2005/0203297 A1 Sep. 15, 2005

Related U.S. Application Data

(60) Provisional application No. 60/552,146, filed on Mar. 11, 2004.

(51) Int. Cl.
*C07D 223/18* (2006.01)
(52) U.S. Cl. .................................................. 540/589
(58) Field of Classification Search ................ 540/589
See application file for complete search history.

(56) References Cited

U.S. PATENT DOCUMENTS

| | | | |
|---|---|---|---|
| 3,642,775 A | 2/1972 | Schindler | |
| 5,808,058 A | 9/1998 | Milanese | |
| 6,670,472 B2 | 12/2003 | Ansari et al. | |
| 2004/0044200 A1 | 3/2004 | Gutman et al. | |

*Primary Examiner*—Brenda L Coleman
(74) *Attorney, Agent, or Firm*—M. Carmen & Associates, PLLC

(57) ABSTRACT

A process for preparing 5H-dibenz[b,f]azepine-5-carboxamide of the general formula:

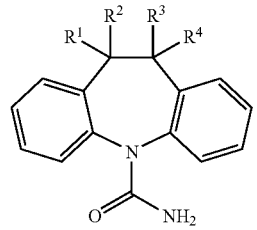

wherein $R^1$, $R^2$, $R^3$ and $R^4$ are the same or different and can be hydrogen, halogen, nitro, cyano, carboxyl, R, —CO(R), —OCO(R), —O(R), —N(R)$_2$, —CON(R)$_2$, and —COO(R), wherein R is selected from the group consisting of $C_1$-$C_{10}$ alkyl, $C_3$-$C_{10}$ cycloalkyl, $C_2$-$C_{10}$ alkenyl, $C_5$-$C_{10}$ cycloalkenyl, $C_2$-$C_{10}$ alkynyl, and $C_6$-$C_{20}$ aryl, wherein the two A groups of —N(A)$_2$ and —CON(A)$_2$ can be the same or different, and wherein $R^2$ and $R^3$ can together form a bond is provided; the process comprising reacting 5H-dibenz[b,f]azepine of the general formula

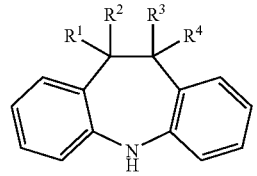

wherein $R^1$, $R^2$, $R^3$ and $R^4$ have the aforementioned meanings, with one or more alkali or alkaline-earth cyanates and in the presence of one or more unsaturated dicarboxylic acids.

34 Claims, No Drawings

PROCESS FOR THE PREPARATION OF CARBOXAMIDE COMPOUNDS

CROSS-REFERENCE TO RELATED APPLICATIONS

This application claims the benefit under 35 U.S.C. §119 to Provisional Application No. 60/552,146, filed Mar. 11, 2004 and entitled "PROCESS FOR THE PREPARATION OF OXCARBAZEPINE", the contents of which are incorporated by reference herein.

BACKGROUND OF THE INVENTION

1. Technical Field

The present invention relates generally to a process for the preparation of carboxamide compounds. More particularly, the present invention relates to a process for preparing 10-methoxycarbamazepine (10-methoxy-5H-dibenz(b,f)azepin-5-carboxamide), an intermediate used in the preparation of 10,11-dihydro-10-oxo-5H-dibenz[b,f]azepine-5-carboxamide (i.e., oxcarbazepine).

2. Description of the Related Art

The present invention relates to a process for the preparation of carboxamide compounds. One such carboxamide compound is oxcarbazepine (also known as 10,11-dihydro-10-oxo-5H-dibenz[b,f]azepine-5-carboxamide of Formula I:

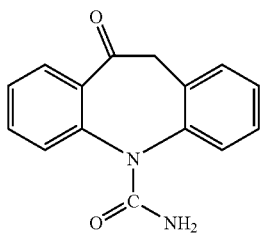

I

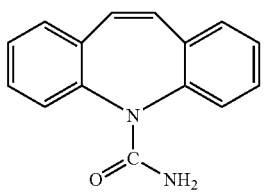

II

Oxcarbazepine is an anticonvulsant drug used in the treatment of epilepsy and is commercially sold under the name Trileptal®. Oxcarbazepine is structurally related to carbamazepine (also known as 5H-dibenzo[b,f]azepine-5-carboxamide of Formula II above, of which oxcarbazepine is a keto derivative. See, e.g., The Merck Index, Thirteenth Edition, 2001, p. 1240, monograph 6998; and Physician's Desk Reference, "Trileptal," 58th Edition, p. 2324-2328 (2003). Oxcarbazepine shares many chemical and pharmacological properties with carbamazepine. Both are highly lipophilic and neutral at most pH values and both are used mainly for the treatment of partial seizures and generalized tonic-clonic seizures. Oxcarbazepine, however, is often used for patients who are intolerant to carbamazepine treatment.

A number of processes to prepare oxcarbazepine are known. For example, U.S. Pat. No. 3,642,775 ("the '775 patent") discloses the synthesis of oxcarbazepine by hydrolysis of 10-methoxy-5H-dibenz[b,f]azepine-5-carboxamide in a dilute mineral acid or in the mixture of water and a water-miscible solvent in the presence of an acid ion exchanger in its acidic form. The synthesis of the starting material 10-methoxy-5H-dibenz[b,f]azepine-5-carboxamide is disclosed in the '775 patent using phosgene gas, which is toxic and subject to strict regulations.

Another example of a process for the preparation of oxcarbazepine is disclosed in U.S. Pat. No. 5,808,058. In this process, 10-methoxy-5H-dibenz[b,f]azepine-5-carboxamide is obtained by carbamoylation of 10-methoxy-5H-dibenz[b,f]azepine with an isocyanic acid generated in situ by the reaction of alkali or alkaline earth cyanates and an acid selected from sulfuric acid, anhydrous hydrochloric acid, anhydrous hydrobromic acid, glacial acetic acid, formic acid, monochloroacetic acid, monobromoacetic acid, dichloroacetic acid, trichloroacetic acid, propionic acid, or 2-chloropropionic acid. The 10-methoxy-5H-dibenz[b,f]azepine-5-carboxamide product is then hydrolyzed with an acid to obtain oxcarbazepine. Alternatively, the hydrolysis can be performed first. However, when an alkali metal cyanate and an acid are added to 10-methoxyiminostilbene, the enol-ether moiety of 10-methoxyiminostilbene undergoes hydrolysis to give the corresponding oxo-iminodibenzyl which does not undergo a carboxamidation reaction with HOCN. Accordingly, the major disadvantage of this process includes competing reactions resulting in the formation of oxo-iminodibenzyl and other impurities, which makes the process less economical.

Yet another example of a process for the preparation of oxcarbazepine is disclosed in U.S. Pat. No. 6,670,472. In this process, 10-methoxy-5H-dibenz[b,f]azepine (10-methoxyiminostilbene) is reacted with a cyanic acid generated in situ by the reaction of an alkali metal cyanate and a mild aromatic acidic reagent such as benzoic acid. The 10-methoxycarbamazepine may then be hydrolyzed to form oxcarbazepine. The major disadvantage of this process includes competing reactions resulting in the formation of oxo-iminodibenzyl and other impurities (see, e.g., Scheme 5), which makes the process less economical.

Accordingly, there remains a need for an improved process for the production of carboxamide compounds such as oxcarbazepine and its intermediates which is economical, safe, and wherein the reaction provides a product in a relatively high yield and high purity.

SUMMARY OF THE INVENTION

In accordance with the present invention, processes for preparing carboxamide compounds are provided. In accordance with one embodiment of the present invention, a process for preparing a 5H-dibenz[b,f]azepine-5-carboxamide of the general formula III:

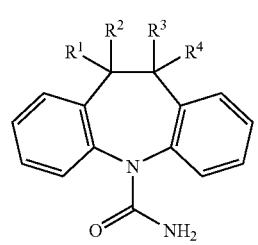

III wherein $R^1$, $R^2$, $R^3$ and $R^4$ are the same or different and can be hydrogen, halogen, nitro, cyano, carboxyl, R, —CO(R), —OCO(R), —O(R), —N(R)$_2$, —CON(R)$_2$, and —COO(R), wherein R is selected from the group consisting of $C_1$-$C_{10}$ alkyl, $C_3$-$C_{10}$ cycloalkyl, $C_2$-$C_{10}$ alkenyl, $C_5$-$C_{10}$ cycloalkenyl, $C_2$-$C_{10}$ alkynyl, and $C_6$-$C_{20}$ aryl, and wherein the two R groups of —N(R)$_2$ and —CON(R)$_2$ can be the same or different, and wherein $R^2$ and $R^3$ can together form a bond is provided; the process comprising reacting a 5H-dibenz[b,f] azepine of the general formula IV:

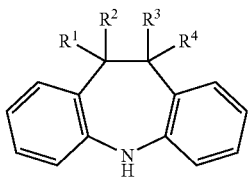

IV wherein $R^1$, $R^2$, $R^3$ and $R^4$ have the aforementioned meanings, with one or more alkali or alkaline-earth cyanates and in the presence of one or more unsaturated dicarboxylic acids.

In accordance with a second embodiment of the present invention, a process for preparing a 5H-dibenz[b,f]azepine-5-carboxamide of the general formula V

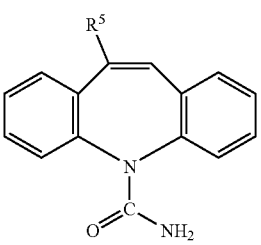

V wherein $R^5$ can be hydrogen or O(R), wherein R is selected from the group consisting of $C_1$-$C_{10}$ alkyl, $C_3$-$C_{10}$ cycloalkyl, $C_2$-$C_{10}$ alkenyl, $C_5$-$C_{10}$ cycloalkenyl, $C_2$-$C_{10}$ alkynyl, and $C_6$-$C_{20}$ aryl, is provided comprising reacting a 5H-dibenz[b, f]azepine of the general formula VI

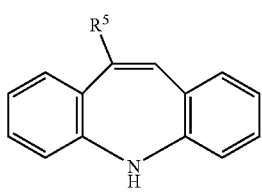

VI with one or more alkali or alkaline-earth cyanates and in the presence of one or more unsaturated dicarboxylic acids.

In accordance with a third embodiment of the present invention, a process for preparing oxcarbazepine is provided comprising reacting a 5H-dibenz[b,f]azepine of the general formula VI

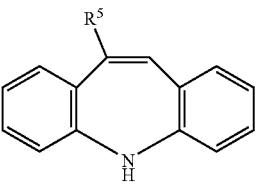

VI wherein $R^5$ is O(R), wherein R is selected from the group consisting of $C_1$-$C_{10}$ alkyl, $C_3$-$C_{10}$ cycloalkyl, $C_2$-$C_{10}$ alkenyl, $C_5$-$C_{10}$ cycloalkenyl, $C_2$-$C_{10}$ alkynyl, and $C_6$-$C_{20}$ aryl, with one or more alkali or alkaline-earth cyanates and in the presence of one or more unsaturated dicarboxylic acids to provide a 5H-dibenz[b,f]azepine-5-carboxamide of the general formula V

V

;

and converting the 5H-dibenz[b,f]azepine-5-carboxamide of the general formula V to provide oxcarbazepine.

In a fourth embodiment of the present invention, a process for preparing oxcarbazepine is provided comprising the carbamoylation of a 10-alkoxyiminostilbene with one or more alkali or alkaline-earth cyanates and in the presence of one or more unsaturated dicarboxylic acids to provide a 10-alkoxycarbamazepine, and hydrolyzing the 10-alkoxycarbamazepine with a dilute acid.

Advantages of the present invention include:

1. The process reduces the time needed and is easier to perform the reactions because it can be performed in a one pot synthesis and has milder reaction conditions.

2. The process is more economical because the same solvent can be used for both the carbamoylation and the hydrolysis steps.

3. By employing an unsaturated dicarboxylic acid, the enol-ether moiety is not rapidly hydrolysed. Therefore, the oxo-iminodibenzyl impurities and other impurities are substantially reduced thereby providing a higher purity and higher yield of the resulting product.

4. The unsaturated dicarboxylic acids are relatively solubile in aromatic hydrocarbon solvents, halogenated hydrocarbon solvents, e.g., aliphatic chlorinated solvents, aromatic chlorinated solvents, etc., making it easier to perform the reactions in solvents. (which also makes it more feasible).

DETAILED DESCRIPTION OF THE PREFERRED EMBODIMENTS

The present invention provides a process for preparing 5H-dibenz[b,f]azepine-5-carboxamides of the general formula III:

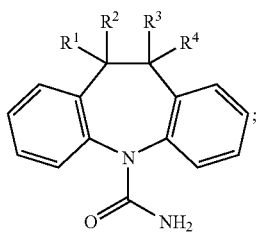

by at least reacting a 5H-dibenz[b,f]azepine of the general formula IV:

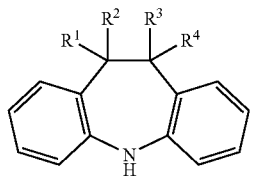

with one or more alkali or alkaline-earth cyanates and in the presence of one or more unsaturated dicarboxylic acids.

Representatives of the $R^1$, $R^2$, $R^3$ and $R^4$ groups, which can be the same or different, include hydrogen, halogen, nitro, cyano, carboxyl, R, —CO(R), —OCO(R), —O(R), —N(R)$_2$, —CON(R)$_2$, and —COO(R), wherein R is selected from the group consisting of $C_1$-$C_{10}$ alkyl, $C_3$-$C_{10}$ cycloalkyl, $C_2$-$C_{10}$ alkenyl, $C_5$-$C_{10}$ cycloalkenyl, $C_2$-$C_{10}$ alkynyl, and $C_6$-$C_{20}$ aryl, and wherein the two R groups of —N(R)$_2$ and —CON(R)$_2$ can be the same or different, and wherein $R^2$ and $R^3$ can together form a bond. Preferably, R is a $C_1$-$C_{10}$ alkyl and more preferably, R is a $C_1$-$C_6$ alkyl.

The above-described alkyl, cycloalkyl, alkenyl, cycloalkenyl, alkynyl, and aryl groups may each be substituted by up to four moieties selected from nitrogen-containing moieties (e.g., amino, amido, etc.), oxygen-containing moieties (e.g., hydroxyl, carboxyl, etc.), halogens, and sulfur-containing moieties (e.g., thiol, sulfonyl, etc.).

Representative examples of $C_1$-$C_{10}$ alkyl groups include, but are not limited to, methyl, ethyl, propyl, isobutyl, 4-(benzyloxy)butyl and the like. Representative examples of $C_3$-$C_{10}$ cycloalkyl groups include, but are not limited to, cyclopentyl, 2-(methyl)cyclohexy, 2-(N,N-(dibenzyl)amino)cyclohexyl and the like. Representative examples of $C_2$-$C_{10}$ alkenyl groups include, but are not limited to, allyl, 2-methyl-2-butenyl, 3-hexen-5-one-2-yl and the like. Representative examples of $C_5$-$C_{10}$ cycloalkenyl groups include, but are not limited to, cyclopentenyl, 4-(isopropyl)cyclohexenyl, 4-(chloromethyl)cyclohexenyl and the like. Representative examples of $C_2$-$C_{10}$ alkynyl groups include, but are not limited to, 2-butynyl, 4-phenyl-2-butynyl, 4-bromomethyl-2-pentynyl and the like. Representative examples of $C_6$-$C_{20}$ aryl groups include, but are not limited to, phenyl, 2-(methyl)naphthyl, 3-(cyano)isoquinolynyl and the like.

Preferably, $R^1$, $R^2$, $R^3$ and $R^4$ are the same or different and can be hydrogen, halogen, R, —OCO(R), —O(R), and —N(R)$_2$, wherein R is selected from the group consisting of $C_1$-$C_{10}$ alkyl, $C_3$-$C_{10}$ cycloalkyl, $C_2$-$C_{10}$ alkenyl, $C_5$-$C_{10}$ cycloalkenyl, $C_2$-$C_{10}$ alkynyl, and $C_6$-$C_{20}$ aryl, and $R^2$ and $R^3$ can together form a bond. More preferably, $R^1$, $R^2$, $R^3$ and $R^4$ are the same or different and can be hydrogen, halogen, —OCO(R), —O(R), and —N(R)$_2$, and $R^2$ and $R^3$ can together form a bond. It is especially preferred that $R^2$ and $R^3$ together form a bond, $R^1$ is hydrogen, and $R^4$ is hydrogen or —O(R), wherein R is selected from the group consisting of $C_1$-$C_{10}$ alkyl, $C_3$-$C_{10}$ cycloalkyl, $C_2$-$C_{10}$ alkenyl, $C_5$-$C_{10}$ cycloalkenyl, $C_2$-$C_{10}$ alkynyl, and $C_6$-$C_{20}$ aryl, with $C_1$-$C_{10}$ alkyl being preferred, $C_1$-$C_3$ alkyl being more preferred and —OCH$_3$ being the preferred example of —O(R).

Accordingly, in another embodiment of the present invention, a process for preparing a 5H-dibenz[b,f]azepine-5-carboxamide of the general formula V:

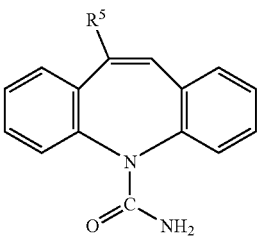

wherein $R^5$ can be hydrogen or O(R), wherein R is selected from the group consisting of $C_1$-$C_{10}$ alkyl, $C_3$-$C_{10}$ cycloalkyl, $C_2$-$C_{10}$ alkenyl, $C_5$-$C_{10}$ cycloalkenyl, $C_2$-$C_{10}$ alkynyl, and $C_6$-$C_{20}$ aryl, is provided comprising reacting a 5H-dibenz[b,f]azepine of the general formula VI

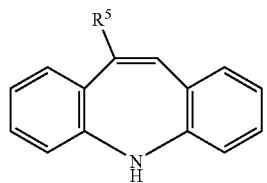

with one or more alkali or alkaline-earth cyanates and in the presence of one or more unsaturated dicarboxylic acids.

In accordance with yet another embodiment of the present invention, a process for preparing a 5H-dibenz[b,f]azepine-5-carboxamide of the general formula V:

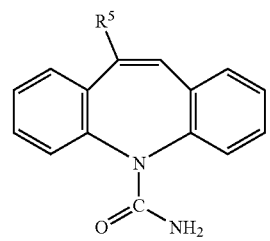

wherein $R^5$ is O(R), wherein R is selected from the group consisting of $C_1$-$C_{10}$ alkyl, $C_3$-$C_{10}$ cycloalkyl, $C_2$-$C_{10}$ alkenyl, $C_5$-$C_{10}$ cycloalkenyl, $C_2$-$C_{10}$ alkynyl, and $C_6$-$C_{20}$ aryl, is provided comprising reacting a 5H-dibenz[b,f]azepine of the general formula VI

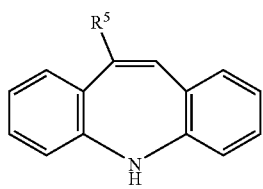

VI with one or more alkali or alkaline-earth cyanates and in the presence of one or more unsaturated dicarboxylic acids.

When $R^5$ is hydrogen, the 5H-dibenz[b,f]azepine-5-carboxamide of formula V is 5H-dibenz[b,f]azepine-5-carboxamide (carbamazepine). When $R^5$ is —O(R) (e.g., —OCH$_3$), the 5H-dibenz[b,f]azepine-5-carboxamide of formula V is a 10-alkoxy-5H-dibenz[b,f]azepine-5-carboxamide, which can be thereafter converted to 10,11-dihydro-10-oxo-5H-dibenz[b,f]azepine-5-carboxamide (oxcarbazepine) by, for example, hydrolyzing with a dilute acid.

Suitable alkali or alkaline-earth cyanates for use in the processes of the present invention include, but are not limited to, sodium cyanate, potassium cyanate and the like and mixtures thereof. The molar ratio of alkali or alkaline-earth cyanates to the 5H-dibenz[b,f]azepine of the general formula IV, e.g., 10-methoxyiminostilbene, will ordinarily range from about 5:1 to about 20:1.

Suitable unsaturated dicarboxylic acids include, but are not limited to, one or more substituted or unsubstituted $C_3$ to about $C_{44}$ unsaturated dicarboxylic acids and preferably one or more substituted or unsubstituted $C_3$ to about $C_{34}$ unsaturated aliphatic dicarboxylic acids and the like. Examples of such unsaturated dicarboxylic acids include, but are not limited to, maleic acid, itaconic acid, fumaric acid, phthalic acid and the like and mixtures thereof. Preferred unsaturated dicarboxylic acids for use herein are maleic acid, fumaric acid and mixtures thereof. The molar ratio of unsaturated dicarboxylic acid to the 5H-dibenz[b,f]azepine of the general formula IV, e.g., 10-methoxyiminostilbene, will ordinarily range from about 1:1 to about 10:1.

The carbamoylation reaction of the foregoing 5H-dibenz[b,f]azepine with one or more alkali or alkaline-earth cyanates and in the presence of one or more unsaturated dicarboxylic acids to produce the 5H-dibenz[b,f]azepine-5-carboxamide may be carried out at a temperature in the range of from about 25° C. to about 50° C. and preferably at a temperature of from about 30° C. to about 35° C. The time period for the reaction can range from about 6 to about 24 hours.

If desired, the carbamoylation reaction can be carried out in an organic medium. The organic medium can be a solvent such as, for example, aromatic hydrocarbon solvents, halogenated hydrocarbon solvents, e.g., aliphatic chlorinated solvents, aromatic chlorinated solvents, etc., and the like and mixtures thereof. Suitable aromatic hydrocarbon solvents include, but are not limited to, toluene, benzene, xylene and the like and mixtures thereof. Suitable halogenated hydrocarbon solvents include, but are not limited to, aliphatic chlorinated solvent such as, for example, methylene chloride, ethylene chloride, trichloroethylene, chloroform, etc., and the like and mixtures thereof. The preferred solvent is methylene chloride. Generally, the ratio of the 5H-dibenz[b,f]azepine of the general formula IV, e.g., 10-methoxyiminostilbene, to solvent will ordinarily range from about 1:5 to about 1:15 w/v and preferably the ratio is about 1:10 w/v.

Following the formation of the intermediate 5H-dibenz[b,f]azepine-5-carboxamides of formula III or V, the intermediate may then be converted to oxcarbazepine. For example, the intermediate 5H-dibenz[b,f]azepine-5-carboxamides of formula III or V can be hydrolysed with a suitable acid, e.g., a dilute mineral acid such as hydrochloric and sulphuric acids, with hydrochloric acid (HCl) being preferred, to produce oxcarbazepine. If desired, following the completion of the carbamoylation reaction, the reaction mixture can first be filtered to separate the inorganic salts utilizing conventional techniques. After the organic layer is separated out, the hydrolysis reaction can then be performed. In an alternate embodiment, the 5H-dibenz[b,f]azepines of formula IV or VI can first be hydrolyzed and thereafter be reacted with the one or more alkali or alkaline-earth cyanates and in the presence of one or more unsaturated dicarboxylic acids to produce oxcarbazepine.

In general, hydrolysis of, for example, the intermediate 5H-dibenz[b,f]azepine-5-carboxamides of formula III or V such as 10-methoxycarbamazepine, can be carried out in a single phase or a biphasic system. When hydrolysis is carried out in a biphasic system, the system is chosen such that oxcarbazepine is substantially insoluble in both phases, whereas the by-products or impurities are soluble in at least one of the phases. The biphasic system includes at least an organic phase and an aqueous phase in which the organic phase is preferably the same solvent used in the carbamoylation reaction, e.g., methylene chloride. Preferably, an excess of this solvent, compared with the amount of impurity or by-product to be produced, is used in the process of this invention. The preferred aqueous phase includes an aqueous solution of at least the acid employed in the hydrolysis step, e.g., dilute hydrochloric acid.

Following the completion of hydrolysis, the oxcarbazepine thus obtained can be purified. For example, the oxcarbazepine can be purified in a mixture of an alcohol and a weak acid. Preferably, purification of oxcarbazepine is carried out in a mixture of methanol and acetic acid. The process of the present invention advantageously provides oxcarbazepine in relatively high purity, e.g., greater than about 95% and preferably greater than about 99%.

In another aspect, the present invention provides a process for preparing oxcarbazepine which comprises carbamoylation of 10-alkoxyiminostilbene with an alkali or alkaline-earth cyanate in a solvent and in the presence of an unsaturated dicarboxylic acid to produce 10-alkoxycarbamazepine, and hydrolyzing 10-alkoxycarbamazepine with a dilute acid to form oxcarbazepine. If desired, following the completion of the carbamoylation reaction, the reaction mixture can be filtered to separate the inorganic salts utilizing conventional techniques. After the organic layer is separated out, the hydrolysis reaction can then be performed as discussed hereinabove.

In a preferred embodiment of the present invention, oxcarbazepine is prepared by carbamoylation of 10-methoxyiminostilbene with potassium isocyanate in the presence of maleic acid, and the resulting 10-methoxycarbamazepine is hydrolyzed with dilute hydrochloric acid as shown in Scheme I:

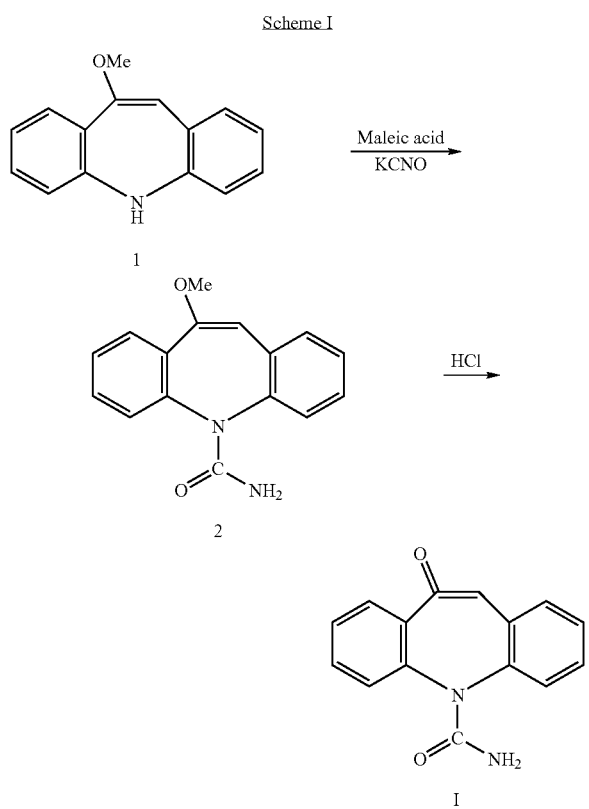

The following examples are provided to enable one skilled in the art to practice the invention and are merely illustrative of the invention. The examples should not be read as limiting the scope of the invention as defined in the claims.

EXAMPLE 1A

Preparation of 10-methoxycarbamazepine

To a 1 L 4-necked round bottom flask was added 10.0 g (0.045 mol) of 10-methoxyiminostilbene, 150.0 ml of dichloromethane, 37.0 g (0.57 mol) of sodium cyanate and 15.0 g (0.13 moles) of maleic acid and stirred at room temperature. The contents were heated to reflux (40-45° C.) under vigorous stirring for about 6 to about 8 hours. After completion of the reaction (detected by TLC) the reaction mass was filtered and washed with 50.0 ml dichloromethane. The dichloromethane layer was washed with water (50.0 ml×2) and the layers were separated.

EXAMPLE 1B

Preparation of Oxcarbazepine

To the organic layer resulting from Example 1A was added 2N HCl (50.0 ml) and the reaction mass was maintained at a temperature ranging from about 40° C. to about 50° C. for about 4 to about 6 hours. After completion of the reaction (detected by TLC) the reaction mass was cooled to a temperature ranging from about 0° C. to about 5° C. for about one hour and the separated solids were filtered and washed with dichloromethane (15.0 ml).

Purification:

To a 3 L 4-necked round bottom flask was added 1125 ml of methanol and 75 gm crude oxcarbazepine prepared by the process of Example 1B and stirred at room temperature, about 25° C. to about 30° C. The reaction mass slurry was heated to reflux, a temperature of about 65° C., and further stirred for about 30 to about 40 minutes. 450 ml acetic acid was added under reflux which resulted in a clear solution. The solution was stirred under reflux at a temperature of about 70° C. for about 30 to about 40 minutes. 7.5 g of charcoal was added to the solution and stirred under reflux for about 20 to about 30 minutes. The reaction mass was filtered and washed twice in a hyflow bed with 75 ml of acetic acid and methanol in a 2:5 ratio at a temperature of about 70° C. The filtrate was cooled in a 3 L 4-necked round bottom flask to a temperature of about 30° C. for about 1 hour, and further cooled to a temperature of about 0° C. for about 30 min. The precipitated product was filtered and dried to get pure oxcarbazepine. Yield=73.0%, m.p. 222° C., purity>99.5%, 1H NMR Spectrum (CDCl3, TMS as internal standard) shows δ at 3.3 (1H,d), 4.4(1H,d), 5.0(2H.br.s), 7.2-8.2 (8H,m&d).

EXAMPLE 2A

Preparation of 10-methoxycarbamazepine 50.0 g (0.224 moles) of 10-methoxyiminostilbene was dissolved in 750.0 ml of dichloromethane. 185.0 g (2.846 moles) of sodium cyanate and 75.0 g (0.65 moles) of maleic acid were added to the above solution at a temperature ranging from about 25° C. to about 30° C. The reaction mass was stirred for about 24 hours. After completion of the reaction (determined by HPLC/TLC) the reaction mass was filtered and washed three times with 100 mL of dichloromethane. The dichloromethane layer was evaporated to get a residue of about 150 g to about 200 g.

EXAMPLE 2B

Preparation of Oxcarbazepine

The residue obtained in Example 2A was transferred to a 2 L 4-necked round bottom flask and 500 ml of 2N aqueous HCl was added at a temperature ranging from about 25° C. to about 30° C. The reaction mass was heated to a temperature ranging from about 80° C. to about 85° C. and maintained for between 4 to 5 hours. After completion of the reaction (detected by HPLC/TLC), the reaction mass was cooled to a temperature ranging from about 50° C., and 500 ml of toluene was charged to the reaction mass and maintained for 30 minutes at a temperature of about 50° C. The reaction mass was further stirred at a temperature ranging from about 25° C. to about 30° C. for about 30 minutes. The solids were filtered, separated, and then washed twice with 100 ml of toluene. The product was dried to get crude oxcarbazepine of 97-98% purity as determined by HPLC.

Purification:

The purification of the oxcarbazepine prepared in Example 2A was carried in substantially the same manner as in Example 1.

While the above description contains many specifics, these specifics should not be construed as limitations of the invention, but merely as exemplifications of preferred embodiments thereof. Those skilled in the art will envision many other embodiments within the scope and spirit of the invention as defined by the claims appended hereto.

What is claimed is:

1. A process for preparing a 5H-dibenz[b,f]azepine-5-carboxamide of the formula:

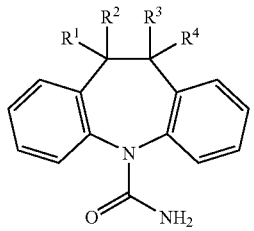

I wherein $R^1$, $R^2$, $R^3$ and $R^4$ are the same or different and can be hydrogen, halogen, nitro, cyano, carboxyl, R, —CO(R), —OCO(R), —O(R), —N(R)$_2$, —CON(R)$_2$, and —COO(R), wherein R is selected from the group consisting of $C_1$-$C_{10}$ alkyl, $C_3$-$C_{10}$ cycloalkyl, $C_2$-$C_{10}$ alkenyl, $C_5$-$C_{10}$ cycloalkenyl, $C_2$-$C_{10}$ alkynyl, and $C_6$-$C_{20}$ aryl, and wherein the two R groups of —N(R)$_2$ and —CON(R)$_2$ can be the same or different, and wherein $R^2$ and $R^3$ can together form a bond; the process comprising reacting a 5H-dibenz[b,f]azepine of the formula

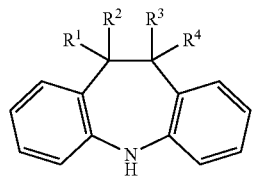

wherein $R^1$, $R^2$, $R^3$ and $R^4$ have the aforementioned meanings, with one or more alkali or alkaline-earth cyanates and in the presence of one or more unsaturated dicarboxylic acid.

2. The process of claim 1, wherein $R^1$, $R^2$, $R^3$ and $R^4$ are the same or different and can be hydrogen, halogen, R, —CO(R), —OCO(R), —O(R), —N(R)$_2$, and —CON(R)$_2$, and wherein $R^2$ and $R^3$ can together form a bond.

3. The process of claim 1, wherein $R^1$ is hydrogen, $R^2$ and $R^3$ together form a bond and $R^4$ is —O(R) wherein R is a $C_1$-$C_{10}$ alkyl.

4. The process of claim 1, wherein the reaction is performed in a solvent.

5. The process of claim 4, wherein the solvent is selected from the group consisting of an aromatic solvent, a halogenated hydrocarbon solvent and mixtures thereof.

6. The process of claim 5, wherein the aromatic solvent is selected from the group consisting of toluene, benzene, xylene and mixtures thereof.

7. The process according to claim 5, wherein the halogenated hydrocarbon solvent is an aliphatic chlorinated solvent selected from the group consisting of methylene chloride, ethylene chloride, trichloroethylene, chloroform and mixtures thereof.

8. The process of claim 1, wherein the one or more alkali or alkaline-earth cyanates are selected from the group consisting of sodium cyanate, potassium cyanate and mixtures thereof.

9. The process of claim 1, wherein the one or more unsaturated dicarboxylic acids comprise a substituted or unsubstituted $C_3$ to about $C_{44}$ unsaturated dicarboxylic acid.

10. The process of claim 1, wherein the one or more unsaturated dicarboxylic acids comprise a substituted or unsubstituted $C_3$ to about $C_{34}$ unsaturated dicarboxylic acid.

11. The process of claim 1, wherein the one or more unsaturated dicarboxylic acids are selected from the group consisting of maleic acid, fumaric acid and mixtures thereof.

12. The process of claim 1, further comprising purifying the product 5H-dibenz[b,f]azepine-5-carboxamide.

13. A process for preparing a 5H-dibenz[b,f]azepine-5-carboxamide of the formula:

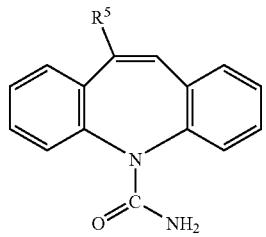

wherein $R^5$ can be hydrogen or O(R), wherein R is selected from the group consisting of $C_1$-$C_{10}$ alkyl, $C_3$-$C_{10}$ cycloalkyl, $C_2$-$C_{10}$ alkenyl, $C_5$-$C_{10}$ cycloalkenyl, $C_2$-$C_{10}$ alkynyl, and $C_6$-$C_{20}$ aryl, is provided comprising reacting a 5H-dibenz[b,f]azepine of the formula:

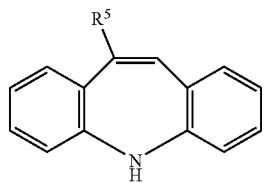

with one or more alkali or alkaline-earth cyanates and in the presence of one or more unsaturated dicarboxylic acids.

14. The process of claim 13, wherein the reaction is performed in a solvent.

15. The process of claim 14, wherein the solvent is selected from the group consisting of an aromatic solvent, a halogenated hydrocarbon solvent and mixtures thereof.

16. The process of claim 13, wherein the one or more alkali or alkaline-earth cyanates are selected from the group consisting of sodium cyanate, potassium cyanate and mixtures thereof; the one or more unsaturated dicarboxylic acids are selected from the group consisting of maleic acid, fumaric acid and mixtures thereof and the reaction is performed in a solvent.

17. The process of claim 13, wherein $R^5$ is —O(R) wherein R is a $C_1$-$C_{10}$ alkyl.

18. The process of claim 13, wherein $R^5$ is —OCH$_3$.

19. The process of claim 17, further comprising hydrolyzing the 5H-dibenz[b,f]azepine-5-carboxamide to produce oxcarbazepine.

20. A process for the preparation of oxcarbazepine of Formula (I):

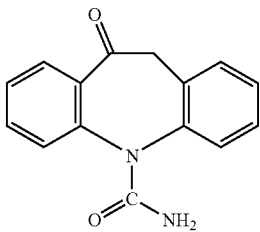

comprising (a) reacting a 5H-dibenz[b,f]azepine of formula II:

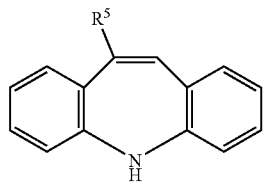

wherein $R^5$ is O(R), wherein R is a $C_1$-$C_{10}$ alkyl, $C_3$-$C_{10}$ cycloalkyl, with one or more alkali or alkaline-earth cyanates and in the presence of one or more unsaturated dicarboxylic acids to provide a 5H-dibenz[b,f]azepine-5-carboxamide intermediate; and (b) hydrolyzing the 5H-dibenz[b,f]azepine-5-carboxamide intermediate to provide oxcarbazepine.

21. The process of claim 20, wherein the one or more alkali or alkaline-earth cyanates are selected from the group consisting of sodium cyanate, potassium cyanate and mixtures thereof.

22. The process of claim 20, wherein the one or more unsaturated dicarboxylic acids comprise a substituted or unsubstituted $C_3$ to about $C_{44}$ unsaturated dicarboxylic acid.

23. The process of claim 20, wherein the one or more unsaturated dicarboxylic acids are selected from the group consisting of maleic acid, fumaric acid and mixtures thereof.

24. The process of claim 20, wherein the reaction is performed in a solvent.

25. The process of claim 24, wherein the solvent is selected from the group consisting of an aromatic solvent, a halogenated hydrocarbon solvent and mixtures thereof.

26. The process of claim 24, wherein the solvent is selected from the group consisting of methylene chloride, ethylene chloride, trichloroethylene, chloroform and mixtures thereof.

27. The process of claim 24, wherein the solvent is selected from the group consisting of toluene, benzene, xylene and mixtures thereof.

28. The process of claim 20, wherein the 5H-dibenz[b,f]azepine-5-carboxamide intermediate is hydrolyzed with a dilute acid.

29. The process of claim 28, wherein the dilute acid is dilute hydrochloric acid.

30. The process of claim 20, further comprising purifying the oxcarbazepine.

31. The process of claim 30, wherein the oxcarbazepine is purified by recrystallization.

32. The process of claim 20, wherein the step of hydrolyzing comprises hydrolyzing the 5H-dibenz[b,f]azepine-5-carboxamide intermediate to oxcarbazepine in a single phase system.

33. The process of claim 20, wherein the step of hydrolyzing comprises hydrolyzing the 5H-dibenz[b,f]azepine-5-carboxamide intermediate to oxcarbazepine in a biphasic system chosen such that the oxcarbazepine is substantially insoluble in both phases, whereas the by-products or impurities are soluble in at least one of the phases.

34. The process of claim 33, wherein the biphasic system comprises an organic phase and an aqueous phase.

* * * * *